United States Patent
Volker et al.

(10) Patent No.: US 9,255,910 B2
(45) Date of Patent: Feb. 9, 2016

(54) SYSTEM AND METHOD FOR PERFORMING ULTRASONIC PIPELINE WALL PROPERTY MEASUREMENTS

(75) Inventors: Arno Willem Frederik Volker, Delft (NL); Joost Gerardus Petrus Bloom, Delft (NL)

(73) Assignee: NEDERLANDSE ORGANISATIE VOOR TOEGEPAST-NATUURWETENS CHAPPELIJK ONDERZOEK TNO, Delft (NL)

( * ) Notice: Subject to any disclaimer, the term of this patent is extended or adjusted under 35 U.S.C. 154(b) by 299 days.

(21) Appl. No.: 13/877,934

(22) PCT Filed: Oct. 7, 2011

(86) PCT No.: PCT/NL2011/050686
§ 371 (c)(1),
(2), (4) Date: Jun. 12, 2013

(87) PCT Pub. No.: WO2012/047107
PCT Pub. Date: Apr. 12, 2012

(65) Prior Publication Data
US 2013/0263667 A1  Oct. 10, 2013

(30) Foreign Application Priority Data

Oct. 7, 2010 (EP) .................................... 10186907

(51) Int. Cl.
*G01B 17/02* (2006.01)
*G01N 29/04* (2006.01)
(Continued)

(52) U.S. Cl.
CPC ................ *G01N 29/07* (2013.01); *G01B 17/02* (2013.01); *G01N 29/04* (2013.01); *G01N 29/4418* (2013.01); *G01N 2291/105* (2013.01); *G01N 2291/2634* (2013.01)

(58) Field of Classification Search
CPC . G01B 17/02; G01N 29/07; G01N 2291/105; G01N 29/04; G01N 29/4418; G01N 2291/2634
USPC .......................................................... 73/598
See application file for complete search history.

(56) References Cited

U.S. PATENT DOCUMENTS

| 4,434,660 A | * | 3/1984 | Michaels et al. | ................ 73/622 |
| 6,047,602 A | * | 4/2000 | Lynnworth | ..................... 73/632 |

(Continued)

FOREIGN PATENT DOCUMENTS

| WO | WO-2008/010306 A1 | 1/2008 |
| WO | 2009139627 A1 | 11/2009 |
| WO | WO-2009/139627 A1 | 11/2009 |

OTHER PUBLICATIONS

Volker, et al; *The Application of Guided Wave Travel Time Tomography to Bends*; journal; 2010; pp. 774-781; vol. 29.

(Continued)

*Primary Examiner* — J M Saint Surin
(74) *Attorney, Agent, or Firm* — Miller, Matthias & Hull LLP

(57) ABSTRACT

Pipeline wall thickness is measured as a function of position using ultrasound propagation. A series of predictive models is used, which define predictions of the ultrasound response signals as a function of different sets of parameters. The different sets that are determine of position dependent ultrasound speed at different sound frequencies and different spatial resolution. Successive iterative fitting process are executed, each fitting a combination of values of a successive set of parameters to the detected ultrasound response signals according to a respective model, using the values fitted values from the previous fitting process to initialize the next set of parameters for iterative fitting. At least the first model defines predictions of wave vector values as a function of circumferential position in successive rings around the pipe as sums of wave vector value for a plurality of circumferential positions in a preceding one of the rings multiplied by propagation coefficients, using propagation coefficients that depend on a first set of parameters.

15 Claims, 5 Drawing Sheets

(51) Int. Cl.
*G01N 29/44* (2006.01)
*G01N 29/07* (2006.01)

(56) References Cited

U.S. PATENT DOCUMENTS

| | | | | |
|---|---|---|---|---|
| 6,487,518 | B1* | 11/2002 | Miyazaki et al. | 702/170 |
| 7,111,516 | B2* | 9/2006 | Bazarov et al. | 73/623 |
| 7,546,224 | B2* | 6/2009 | Campbell | 703/1 |
| 8,225,665 | B2* | 7/2012 | Geir et al. | 73/597 |
| 8,360,635 | B2* | 1/2013 | Huang et al. | 374/147 |
| 8,447,529 | B2* | 5/2013 | Hernandez et al. | 702/25 |
| 2005/0171710 | A1* | 8/2005 | Gysling et al. | 702/54 |
| 2010/0131246 | A1 | 5/2010 | Volker et al. | |
| 2011/0161065 | A1 | 6/2011 | Volker et al. | |
| 2011/0191035 | A1 | 8/2011 | Volker et al. | |
| 2014/0116138 | A1* | 5/2014 | Sheverev et al. | 73/579 |

OTHER PUBLICATIONS

Solie, et al; *Elastic Waves in Free Anisotropic Plates*; journal; Feb. 29, 1972; pp. 50-65; vol. 54, No. 1.

Arno Volker, Erik Luiten, Joost Bloom; The application of guided wave travel time tomography to bends, Review of Quantitative Nondestructive Evaluation, vol. 29, 2010.

* cited by examiner

SYSTEM AND METHOD FOR PERFORMING ULTRASONIC PIPELINE WALL PROPERTY MEASUREMENTS

CROSS-REFERENCE TO RELATED APPLICATIONS

This application is a 35 USC §371 U.S. national stage filing of International Patent Application No. PCT/NL2011/050686 filed on Oct. 7, 2011, which claims priority under the Paris Convention and 35 USC §119 to European Application No. 10186907.1, filed on Oct. 7, 2010.

FIELD OF THE INVENTION DISCLOSURE

The invention relates to a system and method for performing ultrasonic pipeline wall property measurements.

BACKGROUND OF THE DISCLOSURE

From WO 2008/10306 it is known to inspect pipelines for corrosion damage using ultrasonic signals. A transmitter is used to excite an ultrasound wave in the wall of a pipe and a detector is used to detect arrival of the ultrasound wave after it has travelled through the wall.

The information that is obtained in this way can be used to form an image of damage in the pipe wall as a function of position along the wall surface. Properties of the wall are determined from the travel time, i.e. the delay between transmission and arrival. The wall acts as an ultrasound waveguide for waves confined between its inner and outer surface. One can picture wave propagation in terms of a ray that bounces back and forth at an angle to the surfaces, with a net speed of propagation parallel to the surface that depends on the angle. A detector at a specific location on the pipe receives only rays that bounce back and forth at certain discrete angles. At large wavelengths compared to wall thickness, the angle selectivity can be viewed as an effect of constructive interference. At small wavelengths the view is that the rays skip a detector position except at discrete angles.

When pulses of sufficient ultrasound frequency are used, net propagation parallel to the surface gives rise to ray paths that spiral around the pipe, with net axial and circumferential direction components (propagation straight along the axial direction or circularly around the circumference will be considered as special cases of a spiral, with zero circumferential direction component and axial direction component respectively). Typically a detector at a specific location on the pipe will receive rays that reach it along different spiral ray paths, which differ by an integer number of revolutions around the pipe. When the pipe wall has a uniform thickness, the spiral ratio (the ratio between the circumferential and axial direction components) remains constant along such ray paths. The travel time between the time of transmission of a ray and its time of arrival depends on the ray path followed by the ray and the net speed of sound along the ray, which varies with pipe wall thickness.

Local damage to the pipe, which leads to local variation in the pipe wall thickness, results in modulation of the net speed of sound and/or scattering between rays with different spiral ratios. Propagation speed modulation gives rise to modified travel times for combinations of transmitter/detector positions that are connected by ray paths through the location of the local damage. From these travel times, the axial and circumferential location of the damage can be determined. In fact, with arrays of transmitters and detectors, an image of wall thickness variation as a function of position can be obtained. This is called time of flight (TOF) tomography.

WO 2008/10306 discloses a measurement system with ultrasound transducers on a pipe that are used to transmit ultrasound pulses along the wall of the pipe, ultrasound transducers that are used to detect the time of arrival of the ultrasound pulses and a computer that is configured to compute the location of damage from the travel times between the transmitting and receiving transducers. The document mentions that wave dispersion, due to wavelength dependent ultrasound propagation speed, can make the detection of the time of arrival inaccurate. This problem is solved by applying a frequency dependent phase correction to the Fourier transform of the detected ultrasound signal. The result is a sharp pulse, from which the travel time can be determined. Using the resulting travel times for different pairs of transmitting and receiving ultrasound transducers ray paths along the pipe are identified wherein the travel time has changed due to damage.

For the purpose of detecting corrosion damage in the wall of a pipe, high resolution imaging is desirable. At the early stages of pipeline wear corrosion results in small pits that threaten to pierce the wall. High resolution is needed to form images that show such pits. To realize such a high resolution, narrow rays due to ultrasound pulses with frequency content at a relatively high frequency such as 1 MHz are desirable. However, it has been found that at such frequencies it is difficult to compute a reliable tomographic image. The images often show artefacts. It has been found that these artefacts are due to convergence of the tomographic reconstruction to local maxima.

WO2009139627 also discloses modelling of the surface of an object, such as a pipe, using ultrasonic waves. Propagation delay times obtained from ultrasonic measurements are compared with predictions based on a model of the surface. Both surface height and temperature parameters of the model are iteratively adapted. Inclusion of temperature as a parameter makes it possible to account for refraction, where the time delay corresponds to a bent ray path that deviates from the ray path at homogeneous temperatures. Non dispersive waves are used, such as waves that are concentrated in a single narrow frequency band. The propagation delays are modelled by treating ultrasound propagation as propagation along a ray path. No wave vector summation or wave interference computations are considered. A two level model is used, wherein the height and temperature of a limited number of points is adapted and values for other points are obtained by interpolation.

SUMMARY OF THE DISCLOSURE

Among others it is an object to provide for a system and method for performing ultrasonic pipe wall thickness measurements wherein a more reliable convergence is made possible.

A method according to claim 1 is provided. Herein a first and second iterative model fitting processes are used, a set of fitted parameter values from the first model fitting process used to initialise the parameter values to be fit in the second process. The model fitting processes use sets of parameters that determine at least the speed of sound in the wall of the pipe as a function of position along the wall surface. The second process uses detected transmission at one or more higher sound frequencies than the first step and a set of parameters that determines the position dependence of the speed of sound at higher spatial resolution.

By using an initial first iterative model fitting process at low sound frequency and low spatial resolution, the risk can be reduced that the second process converges to a local optimum. The initial first iterative model fitting process is applied to a sound frequency that is so low that it would not normally be used for imaging because prediction of transmission based on travel time along ray paths is insufficiently accurate at this sound frequency. To ensure that the initial first iterative model fitting process provides usable initial parameters for the second model fitting process, initial first iterative model fitting process uses wave vector value that are each computed from sums of wave vector value for a plurality of circumferential positions in a preceding ring around the pipe, multiplied by propagation coefficients, using propagation coefficients that depend on the sound speed as a function of position as defined by the first set of parameters. Thus, the predictions are computed using wave vectors that account for wave fronts distributed over a width of more than one sampling position rather than individual ray paths. The first frequency may be 50 kHz or lower for example.

In an embodiment a series of predictive models is used, the fitted parameter values of each fitting process being used to initialize the parameter values of the next fitting process, if any. In this embodiment successive process for fitting at successive higher respective sound frequency, or sound frequencies up to the respective sound frequency, the respective sound frequencies and the respective spatial resolutions increasing for successive further predictive models in the series. In this way a large sound frequency gap and a corresponding spatial resolution gap between the initial first model fitting process and the last process can be closed. The sound frequency of the initial first model fitting process may be 50 kHz or lower and the sound frequency of the final model fitting process may be 500 kHz or higher for example, in which case models at five or more different frequencies and spatial resolutions may be used.

In an embodiment the model or models at frequencies above a predetermined frequency may be based on integrating travel times along the paths dependent on the position dependent ultrasound speed determined by model parameters, without using sums of contributions from positions on a preceding ring.

In an embodiment, the pipeline has a bent section between the ultrasound transmitters and the ultrasound transmitters. In a further embodiment models using sums of contributions from positions on preceding rings may be used for all frequencies for such a bent section. In this case, integrating travel times along the paths may be used for straight pipe sections, at least for frequencies above a predetermined frequency.

In an embodiment the transmitters and receivers may be coupled to the pipeline along a first and second circumferential ring in planes transverse to an axial direction of the pipeline respectively, in each of the first and second ring at mutually spaced circumferential positions. This makes it possible to form an image of the entire pipe wall between the rings.

In an embodiment the pipeline is supported by a support having a contact with the pipeline, the transmitters and receivers being coupled to the pipeline at mutually spaced circumferential positions along an line in the axial direction of the pipeline, transmitters and receivers being coupled to the pipeline on mutually opposite sides of the contact respectively. This makes it possible to assess damage specifically at the contact to the support.

In an embodiment the transmitted ultrasound signals are wideband signals comprising components at both the first and second frequencies, the first and second fitting process being applied to selected frequency components of the detected ultrasound response signals. In this way a single type of pulse may suffice to form images.

A system for performing the method is also provided, as well as a computer program product, such as a magnetic or optical disk or a semiconductor memory, comprising a program of instructions for a programmable computer that, when executed by the computer will cause the computer to perform the method of any one of the preceding method claims.

BRIEF DESCRIPTION OF THE DRAWING

These and other objects and advantageous aspects will become apparent from a description of exemplary embodiments, using the following figures

DETAILED DESCRIPTION OF EXEMPLARY EMBODIMENTS

Figure 1:
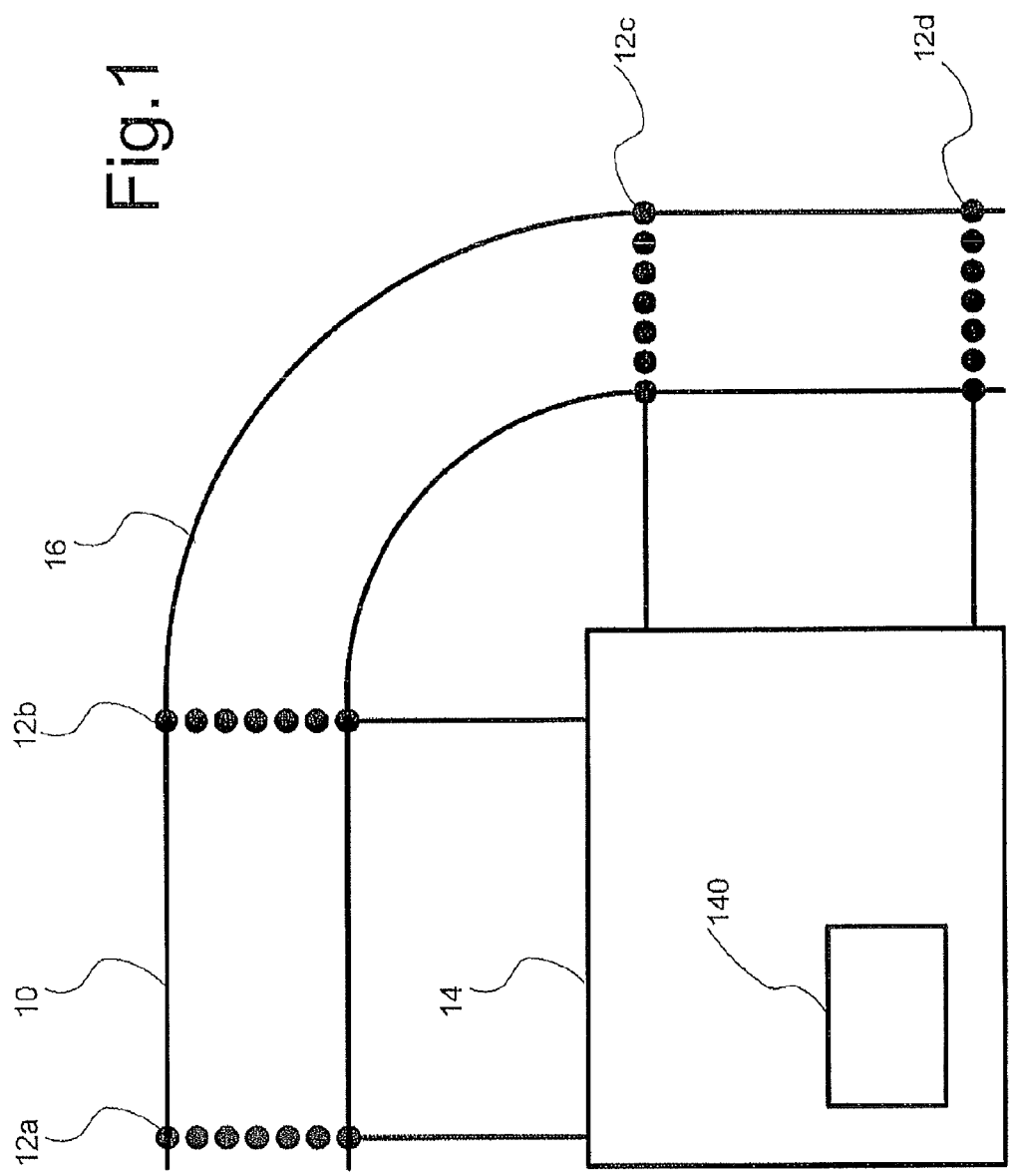
FIG. 1 shows a measuring system

FIG. 1 shows a pipeline wall thickness measuring system comprising a pipeline 10 with rings of ultrasound transducers 12a-d coupled to pipeline 10 and an excitation and detection circuit 14 coupled to ultrasound transducers 12a-d. Excitation and detection circuit 14 comprises a signal processing circuit 140. Alternatively, a separate signal processing circuit, such as a computer programmed to perform signal processing may be coupled to excitation and detection circuit 14. Each ring extends circumferentially around pipeline 10 at a respective axial position. Each ring has a plurality of ultrasound transducers 12a-d at respective positions along the circumference at that axial position. As shown pipeline 10 has a bend 16, with rings of ultrasound transducers 12a-d on pipeline sections on both sides of the bend. In another embodiment one or more rings of ultrasound transducers 12a-d may be provided in bend 16.

Figure 2:
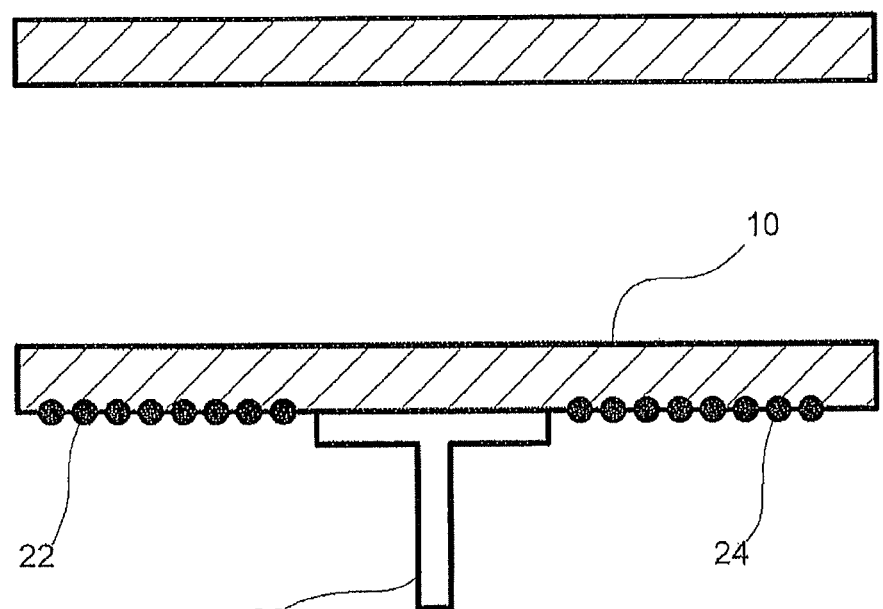
FIG. 2 shows a transducer configuration

FIG. 2 shows an alternative pipeline wall thickness measuring system in a cross-section. Part of a pipe 10 and a pipe support 20 connected to pipe 10. A first series of ultrasound transducers 22 is provided at successively different axial positions on a first axial side of support 20. A second series of ultrasound transducers 24 is provided at successively different axial positions on a second axial side of support 20, opposite the first side.

Ultrasound transducers 12a-d, 22, 24 are devices capable of transmitting ultrasound vibrations to the wall of pipeline 10 and/or detecting such vibrations in the wall, when controlled to do so. Detection may comprise generating an electrical response signal that varies in proportion to displacement in the wall due to ultrasound waves. Excitation and detection circuit 14 is configured to control ultrasound transducers 12a-d, 22 to excite ultrasound waves at selected positions in the wall of pipeline 10 and to receive back response signals due to the arrival of resulting ultrasound waves at other positions in the wall, using other transducers 12a-d, 24.

In the example of FIG. 1, excitation and detection circuit 14 may be configured to control respective ultrasound transducers 12a-d in a first ring successively to excite distinct ultrasound waves in pipeline 10 from each of these ultrasound transducers 12a-d respectively, and to receive resulting detected ultrasound signals from transducers 12a-d in a second ring. Thus, ultrasound transmission response function between individual pairs of transducers 12a-d may be detected.

Figure 3:
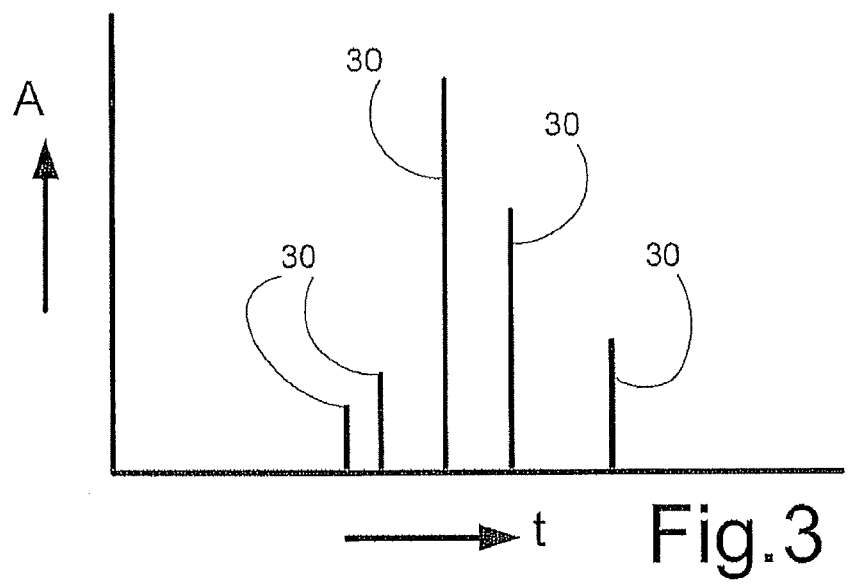
FIG. 3 illustrates a theoretical amplitude response as a function of time

FIG. 3 illustrates a theoretical amplitude response as a function of time for ultrasound transmission through a straight section of pipeline 10 of uniform thickness. In this example, the amplitude response represents ultrasound vibration amplitude "A" as a function of time "t" from the time of transmission of an ultrasound pulse with frequencies in a narrow frequency band. As can be seen, the response comprises a number of discrete peaks 30, at distinct discrete temporal positions. In a first approximation, each peak corresponds to the travel time of sound that has travelled along a ray path in the wall of pipe 10 from the location of a transmitting transducer 12a-d to a location of a receiving transducer 12a-d, with a delay corresponding to the length of the ray path and the speed of sound in the ray path.

Figure 3A:
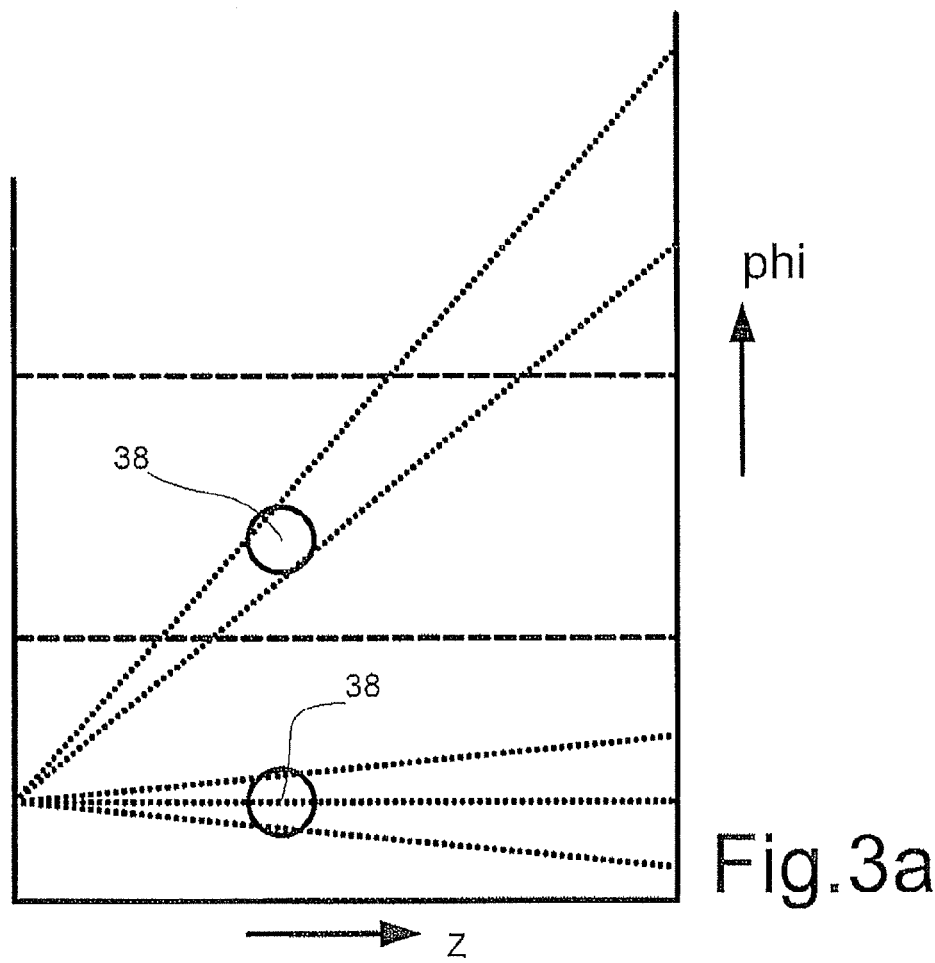
FIG. 3a illustrates the ray paths.

FIG. 3a illustrates the ray paths. The axial coordinate "z" of locations on pipe 10 is plotted horizontally and the circumferential coordinate "phi" of these locations is plotted vertically. Examples of ray paths in a straight section of pipe 10 are indicated by dotted lines. A horizontal dotted line corresponds to an axial ray path and oblique dotted lines correspond to ray paths that spiral around the axis of pipe 10. For the sake of exposition, the circumferential coordinate in the vertical direction is unfolded: circumferential coordinates repeat after each revolution around pipe 10, but in the figure successive coordinates after a repetition are shown as if they continue. Thus, the same positions on the wall are shown repeatedly in vertically successive horizontal strips, separated by dashed lines. A spiralling ray path can thus be shown as a continuous straight line, even though its circumferential coordinate repeats in 360 degree cycles.

By way of example it may be assumed that the left vertical of the figure corresponds to the axial coordinate of a ring of transmitting ultrasound transducers 12a-d and the left vertical of the figure corresponds to the axial coordinate of a ring of receiving ultrasound transducers 12a-d. Because of the unfolding, the position of the same ultrasound transducer 12a-d is shown repeatedly in the successive horizontal strips. Each peak in FIG. 3 corresponds to the time of arrival of an ultrasound wave along a ray path that can be shown as a straight line between positions of the transmitting and receiving ultrasound transducers 12a,b. Because of the repetitive nature of the vertical coordinate of FIG. 3a, the same transmitting and receiving ultrasound transducers 12a,b may be connected by a plurality of ray paths, that differ by the number of times that the ray path has spiralled around the circumference of pipe 10 before reaching the detecting transducer The travel times shown in FIG. 3 depend on the length of the ray path and on the speed of ultrasound propagation through the wall of pipeline. The speed of ultrasound propagation depends on wall thickness, which defines the properties of waveguide modes of the waveguide formed between the inner surface and the outer surface of the wall of pipe. A plurality of different waveguide mode of the ultrasound waveguide may occur, with different propagation speed. As a result, the same ray path may give rise to a plurality of different travel times.

When the wall thickness varies locally due to damage to pipe 10 this gives rise to a local change of the propagation speed that shifts the positions of peaks 30 obtained with those pairs of transducers 12a-d that are connected by ray paths through a region with locally different wall thickness. If the speed of sound in a region 38 of the pipe wall differs from that of the remainder of the pipe wall, sound propagation through ray paths that pass through region 38 will be detectably affected. FIG. 3a shows ray paths from one transmitting ultrasound transducer to from receiving ultrasound transducers that are affected by propagation through region 38. For the receiving ultrasound transducers at the end of such ray paths the time of arrival of ultrasound pulses from the transmitting ultrasound transducer will be changed.

In principle the shift this makes it possible to determine the circumferential and axial position of the region 38 with different speed of sound from the measured travel times between ultrasound transducers. The position must be at cross sections between ray paths between pairs of ultrasound transducers 12a-d that show a shifted peak. The size of the wall thickness change can be determined from the amount of shift of the peaks.

The preceding applies to straight sections of pipe 10. The effect in a bend 16 is more complicated. In principle, one can draw rays paths for locations in a bend 16 in a diagram like that of FIG. 3a. These ray paths will be curved rather than straight, dependent on the geometry of the bend 16. One may try to modify the procedure for determining the locations of regions with deviating speed of sound in straight sections by applying measured travel times to such curved ray paths instead of to the straight ray paths.

Travel time tomography can be used to form an image of the speed of sound as a function of position on the pipe. The image describes wall thickness, or one or more sound propagation properties that depend on wall thickness as a function of position along the surface of the wall. Given an image, the corresponding travel times for respective pairs of transceivers can be predicted. In an embodiment of travel time tomography, a processor compares the predicted travel times with the measured travel times. The result of the comparison may be computation of a difference measure, e.g. a sum of squares of the differences between the measured and predicted travel times of different pairs of transducers, plus optional regularization terms that represent the apriori likelihood of selectable tomographic images. The difference measure is used to select updates to the image that reduce the difference measure. This is repeated iteratively until the iterations converge to an image that yields a minimum or near minimum difference measure.

To obtain images with sufficient resolution to detect corrosion damage to the pipe, high resolution images are desirable. Corrosion initially leads to narrow pits, which must be detected. Pulses with high ultrasound frequencies, for example 1 MHz, and iterative adaptation of the image to the travel times of pulses with such a frequency content are needed to realize the required resolution. However, it has been found that when such high frequencies are used, at least in some cases the application of the iterative process to derive the images from the measured travel times does not lead to sufficiently reliable images. It was found that this was because the iterations converge to local minima, which do not represent images that are useful for detecting damage to the pipe. Curved ray paths in a bend may also give rise to problems. It has been found that a bend also gives rise to ultrasonic lens effects and that these effects affect the reliability of the detection of damage.

It has been found that this problem can be overcome by starting the iterations from an initial estimate that is obtained using such low ultrasound frequencies at which the ray path approximation does not give accurate images, even at low resolution. 50 kHz ultra sound frequency content may be used for example.

Figure 4:
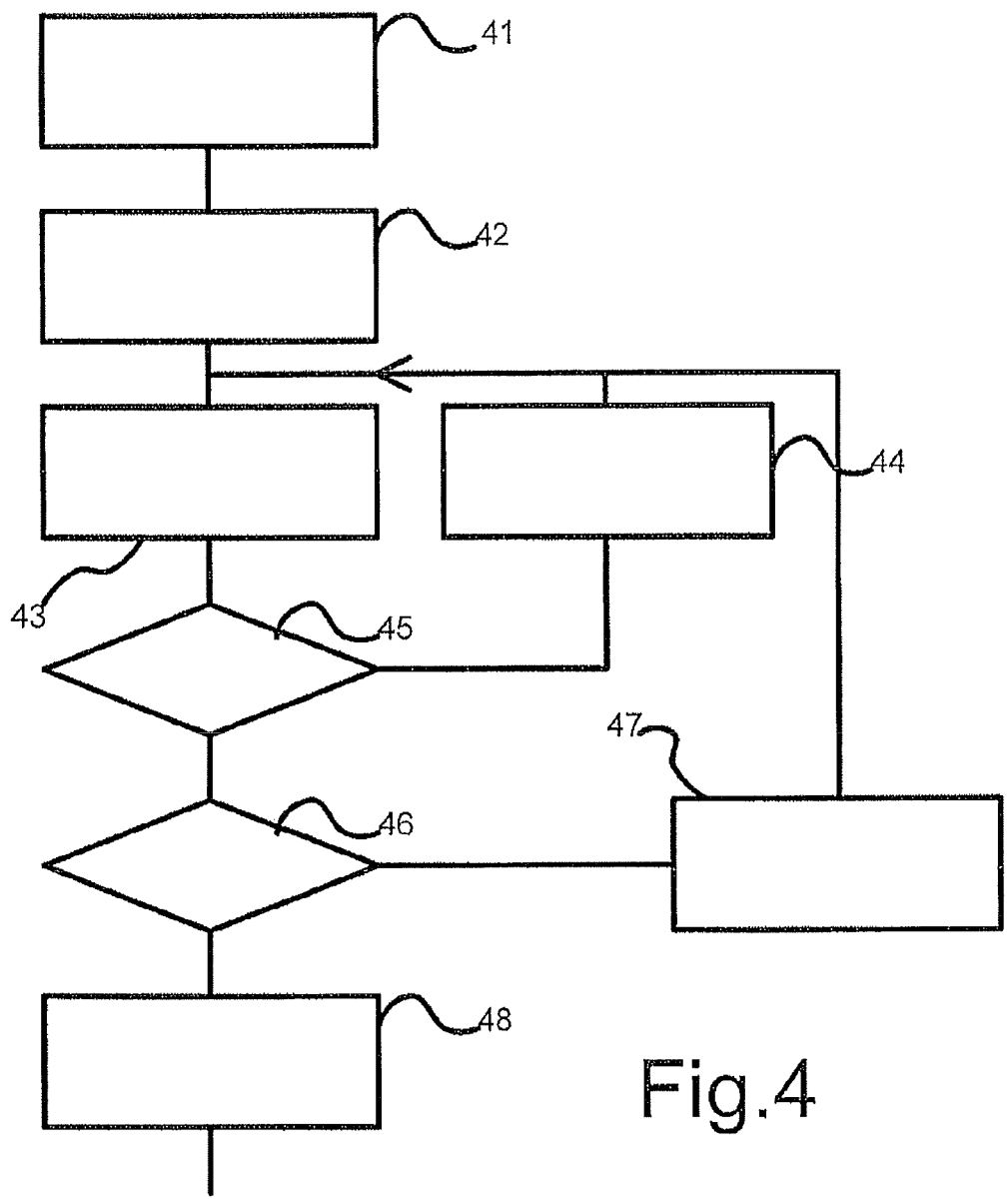
FIG. 4 shows a flow chart of the process of parameter adaptation

FIG. 4 shows a flow chart of the process of parameter adaptation. In a first step 41 the signal processing circuit 140 of excitation and detection circuit 14 (or a signal processing circuit 140 coupled to excitation and detection circuit 14) obtains ultrasound transmission response functions between pairs of ultrasound transducers 12b,c in the first and second ring respectively, by successively controlling different ultrasound transducers 12b in the first ring to excite ultrasound waves in pipe 10 and receiving measured ultrasound signals subsequent to the excitations from ultrasound transducers 12c in the second ring in time windows at a predetermined time relative temporal position with respect to the excitations. The measured ultrasound signals represent ultrasound displacement in the wall of pipe 10 as a function of time, that is, not just the timing but also the size of displacement.

In an embodiment, wide band ultrasound pulses are transmitted with a frequency content covering a range of 50 kHz to 1 MHz for example. Preferably, the frequency range includes frequencies at which the ultrasound wavelength in the wall of pipe 10 is larger than the thickness of the wall, up to frequencies where the wavelength is smaller than the thickness. The result is a set of response functions of the ultrasound vibration amplitude as a function of time, each for a respective pair of ultrasound transducers 12b,c in the first and second ring. The response functions may be Fourier transformed to obtain components at different frequencies. An FFT may be used for example. In another embodiment a series of more narrow band ultrasound pulses may be transmitted with a frequency content at respective frequencies in this range. In this embodiment phase and amplitude and optionally travel time of the response to each of these pulses at the receiving transducers 12c may be measured.

In a second step 42 signal processing circuit 140 sets an initial bandwidth setting W and initial values of wall thickness parameters. In an embodiment the initial bandwidth selects a single measurement frequency (component) of 50 kHz for example. In an embodiment, the wall thickness parameters may represent a thickness image with "pixels" that correspond to at a 2 dimensional set of sampled positions along pipe 10 distributed over a position range from the first ring to the second ring in a first dimension and around the circumference of pipe 10 in a second dimensions. Values defining a uniform thickness may be used as initial values for example, or thickness measured at an earlier time. In an embodiment, the bandwidth setting W is used to indicate a sub-sample rate that defines sub-set of the set of sample positions at sub-sampled positions. In this embodiment the values of the parameters for the remaining sample points may be interpolated between the values for the sub-sampled positions.

Third to fifth steps 43-45 correspond to a computation stage in which a fitting process at the selected bandwidth setting W is performed. The fitting process at the selected bandwidth setting W comprises iterations of update steps.

In a third step 43 signal processing circuit 140 computes predicted response functions between pairs of transducers 12b,c in the first and second ring for a pipe with a position dependent wall thickness according to the wall thickness parameters. For the computation wall thicknesses between the sampled positions may be defined by interpolation between the sampled positions. Furthermore in third step 43 signal processing circuit 140 computes a difference between the predicted response functions and the measured response functions. In an embodiment, the computation of the predicted response functions is computed dependent on the bandwidth setting W. In one embodiment, the predicted response is computed for a single frequency at the highest point of the bandwidth W and the difference is computed with the measured response at that frequency. In another embodiment, the predicted response is computed for a combination of frequencies up to the bandwidth and the difference is computed with a combination of responses up to the bandwidth.

In an embodiment the predicted responses between pairs of transducers for frequencies above a predetermined minimum frequency may be computed using a ray path approximation, that select paths between the pairs of transducers and integrates the effects of the thickness along the paths, as defined in the thickness image. An embodiment of the computation of the prediction for lower frequencies will be described in more detail in the following.

In this embodiment, which is used at least at the lowest frequency (50 kHz for example) the computation of the prediction is performed using a thickness dependent propagation operator rather than by using travel times along ray paths between pairs of transducers only.

In this embodiment of the computation, successive virtual rings of sampled positions along pipe 10 are defined. Each virtual ring comprises a plurality of sampled positions along the circumference of pipe 10. Successive virtual rings are located at successive axial sample coordinates. In bend 16, the directions of the virtual rings diverge, radiating from a notional centre of curvature of the bend 16. Thus the sample positions in successive virtual rings on the outside of the bend lie further apart than on the inside of the bend.

In this embodiment, a wave vectors (amplitude and phase) at the computation frequency (e.g. 50 kHz) is computed for the position of a given transmitting transducer 12b in the first ring and a set of wave vectors is computed for sampled positions on a first virtual ring between first and second ring of ultrasound transducers 12b, c. Subsequently, successive wave vectors for the computation frequency in other rings are determined for sampled positions on virtual rings of sampled positions that are successively closer to the second ring of ultrasound transducers 12c. For each respective sampled position in a next (e.g. virtual) ring, the successive wave vector is determined from a sum of contributions of different source sampled points on the preceding (e.g. virtual) ring, multiplied by coefficients that are selected dependent on the speed of sound c(r) at the next ring, at the preceding ring or between the next ring and the preceding ring, at the circumferential position of the respective sampled position in the next ring, according to the model parameters (e.g. according to the thickness image). This applies when only one propagation mode in the pipeline walls is used. When propagation in the wall supports a plurality of modes with different speeds of sound, respective wave vectors for each of these modes may be computed, each in the same way as a for a single mode. In this case, the relative amplitudes of different wave vectors in the initial ring may be determined from predetermined relative input coupling factors for the different modes. The total output at the receiver may be computed using predetermined relative output coupling factors for the different modes. The relative input and output coupling factors for the different modes may be determined using calibration measurement for a standard pipe section.

Coefficients are used that depend on the circumferential positions of the respective sampled position in the next ring for which the wave vector is determined and the different source sampled points on the preceding ring. Along a straight section of pipe 10 the coefficients depend only on the difference between the circumferential positions of the sampled point for which the wave vector is determined and of the source sampled points. But in bend 16 the coefficients also depend on the individual circumferential positions of these points (not just their relative position), for example because the distance between sampling points on successive rings is smaller on the inside of the bend than on the outside.

The dependence of the coefficients F on the circumferential position on the preceding ring may be represented by a Fourier transform of this dependence. The Fourier transform of the dependence on circumferential position defines Fourier transform coefficients at circumferential spatial frequencies Fc=2*pi*R//L, where R is the radius of the pipe and L is a circumferential wavelength. In principle, for a given speed of sound "c" when a single ultrasound mode is used, this Fourier transform of the coefficients F may be taken to have the value $$F(L,c)=\exp(-i*2*pi*k*h) \text{ with } k=\text{sqrt}((f/c)^2-1/L^2)$$

Herein i is a square root of −1: $i^2=-1$, h is the distance between successive rings of sampling points (at the circumferential position of the sampling point in the next ring in the case of a bend), f is the sound frequency for which the wave vector is computed.

The coefficients F(Rs, c) as a function of circumferential position Rs along the preceding ring may be determined by computing the inverse Fourier transform. However, use of exactly this coefficient obtained from inverse Fourier transform has the disadvantage that all source sampling points in the preceding ring need to be used for each sampling point for which the wave vector is determined. In a further embodiment, the amount of computations is reduced by making the coefficients F(Rs, c) zero for all but source sampling points at circumferential positions Rs that are less than a predetermined distance away from the circumferential position of the sampling point for which the wave vector is determined. In other words, the sum over source positions at different circumferential positions in the preceding ring is extended only over a predetermined limited range of circumferential positions, containing the circumferential position of the point for which the wave vector is computed in the next ring and at least one further circumferential position in the preceding ring on either side. Non-zero coefficients for source sampling points at at least three circumferential positions are used for example, and preferably more.

In this case, the remaining non-zero coefficients F(Rs, c) may be adapted in order to improve numerical stability. Techniques for doing so are known per se. Numerical stability can be judged from a renewed Fourier transform of the coefficients after making part of them zero, and a determination whether the absolute values of the resulting Fourier transform coefficients exceeds one. An excess over an absolute value of one is preferably suppressed, or at least made small. An optimization method may be used, wherein the non-zero coefficients are chosen so that they minimize a target function which increases with increased deviation from the factors F above, giving higher weight in the target function to deviations that raise the absolute value above one than to deviations that do not do so. Tables of the factors may pre-stored and used in the computation.

The prediction of the response functions is available once the computation of the wave vectors has been repeated for successive virtual rings until the position of the second ring of ultrasound transducers 12b has been reached.

Summarizing, in third step 43, signal processing circuit 140 computes predicted response functions between pairs of transducers 12b,c in the first and second ring for a pipe with a position dependent wall thickness. according to the wall thickness parameters. For at least the lowest frequency (e.g. 50 kHz) the computation of the predicted response functions comprises computing wave vectors (amplitude and phase) for sets of sample points in successive series of circumferential positions along successive virtual rings along the pipe. The first ring comprises the location of the transmitting transducer and the last ring comprises the position of the receiving transducer. The values of the wave vector in the first ring are taken to be zero at all circumferential positions except that of the transmitting transducer.

In succeeding virtual rings wave vectors is computed for the position of a given transmitting transducer 12b in the first ring and a set of wave vectors is computed for sampled positions on a first ring 12b between first and second ring of ultrasound transducers 12b, c. Subsequently, successive wave vectors are determined for sampled positions on virtual rings of sampled positions that are successively closer to the second ring of ultrasound transducers 12c. For each respective sampled position in a next ring, the successive wave vector is determined from a sum of contributions of different source sampled points on the preceding ring, multiplied by coefficients that are selected dependent on the speed of sound c(r) at the next ring, at the preceding ring or between the next ring and the preceding ring, at the circumferential position of the respective sampled position in the next ring, according to the model parameters (e.g. according to the thickness image). This repeated until the wave vector at the positions of the receiving transducers in second ring 12c has been determined. This is done for all transmitting transducers and if need be for all contributing modes of propagation. For frequencies above a threshold frequency, the predictions may be computed by selecting ray paths between transmitting and receiving transducers and adding travel times determined from the thickness image along the ray path. Furthermore in third step 43 signal processing circuit 140 computes a difference between the predicted response functions and the measured response functions. Instead of direct determination of a difference, other types of comparison may be used. For example, logarithms of the response functions may be subtracted, or a ratio of the predicted response functions and the measured response functions and compared to reference value. If the absolute values of the input and output coupling factors that relate transmitting and receiving transducer signals to ultrasound displacement in the pipe wall are not known, the difference may be computed after applying a correction factor that minimizes the overall difference. Generally, the results of such comparisons will be referred to as differences.

In a fourth step 44 signal processing circuit 140 determines whether the difference meets a convergence criterion. The convergence criterion may depend on the bandwidth setting W. In a first embodiment, only the difference between the measured and predicted wave vectors for a highest frequency component at or below the bandwidth is determined. In another embodiment only the difference between the measured and predicted wave vectors of a combination of frequency components (e.g. all) at or below the bandwidth is determined, for by summing difference measures for different frequencies. The higher frequency components of the differences outside the bandwidth setting W are suppressed in the computation of the convergence criterion, at least relative to frequency components of the difference within the bandwidth setting W.

If the difference does not meet the convergence criterion, signal processing circuit 140 executes a fifth step 45, selecting adapted values of the parameters, based on the difference and repeats from third step 43. The selection of the adapted values may be controlled dependent on the bandwidth setting W. In the embodiment with sample points and sub-sampling, only the values for a sub-sampled set of sample points are updated directly, and the values of the parameters for the remaining sample point may be interpolated.

If the difference meets a convergence criterion, signal processing circuit 140 executes a sixth step 46, wherein it determines whether the bandwidth setting W is lower than a maximum value Wmax. If so, signal processing circuit 140 executes a seventh step 47, wherein it increases the bandwidth setting W and performs a new stage of fitting, at the new bandwidth setting W, repeating from third step 43. In this case, the parameter values (e.g. thickness image) computed with the old bandwidth setting W serve as initial parameter values in third step 43. In an embodiment at least at the lowest bandwidth setting the initial parameter values (e.g. thickness image) are computed using propagators instead of ray paths.

In the embodiment with sample points and sub-sampling, the increase of the bandwidth setting W increases the number of sub-sampled sampling points and the initial values of the parameters for the new sub-sampled sampling points are determined by interpolation.

If signal processing circuit 140 determines in sixth step 46 that the bandwidth setting W has reached or exceeded the maximum value Wmax, signal processing circuit 140 executes an eight step 48, outputting information derived from the values of the parameters. An image may be displayed for example, indicating computed wall thickness as a function of position along pipe 10 as a function of position in the image.

The measures signals represent measured displacement (amplitude) in the wall of pipe 10 due to ultrasound waves at a plurality of frequencies in addition to the travel times, at least for bent sections of pipe 10. That is, not only travel times, but also amplitude is used. The response signals as a function of time, will be sinusoids in the case of continuous wave excitation. In the case of pulsed excitation, it is a sum (integral) of sinusoids for different wavelengths in the wall of pipe 10. For the application to straight section, these ultrasound displacement amplitudes may also be used, but in this case and at higher frequencies it may instead suffice to use only the travel times associated with response pulses that result from excitation pulses.

In the embodiment of FIG. 1, signal processing circuit 140 processes the ultrasound transmission response function between individual pairs of transducers in successive rings of ultrasound transducers 12a-d to form an image of pipe wall thickness as a function of position on pipe 10. The ultrasound transmission response function over a wide band of ultrasound frequencies is used, for example from 50 kHz to 1 Mhz. Preferably, the frequency range includes frequencies at which the ultrasound wavelength in the wall of pipe 10 is larger than the thickness of the wall up to frequencies where the wavelength is smaller than the thickness. Signal processing circuit 140 is configured to use a parameter fitting process for values of a set of parameters that describe sound propagation speed as a function of position on pipe 10, for example in terms of pipeline wall thickness.

In an iterative fitting process, the set of parameters is used to compute predictions of the ultrasound transmission response functions, including ultrasound vibration amplitude. Signal processing circuit 140 compares these predictions with the detected ultrasound transmission response functions, including ultrasound vibration amplitude. A result of the comparison is used to adapt the values of the parameters. The prediction, comparison and adaptation are repeated until a convergence criterion is met. The final values of the parameters are used to output as description of estimated pipeline wall thickness.

At least at one or more lowest frequencies, propagators are used to compute the predictions. This makes is possible to ensure convergence. By using very low frequencies an initial low resolution image can be made. At low frequencies the reliability of the image is increased by comparing with predictions computed using propagators. This is especially so when bent pipe sections are included. In an embodiment, predictions for all frequencies are computed using propagators for bent pipe sections. That is, for the first and second ring of ultrasound transducers 12b,c which are separated by bend part 16, the fitting process fits the ultrasound displacement as a function of time or frequency and not just the shift of times of arrival of pulses. Thus, the comparison that is used to adapt the values of the parameters comprises comparison of transmission amplitude information that is redundant for mere comparison of travel time information. As a result it is possible to perform more accurate detection.

For the computation of the difference between the predicted response functions and the measured response function, a temporal Fourier the measured response functions for each pair of ultrasound transducers 12b,c may be computed. This results in sets of Fourier coefficients for different frequencies, which may be compared with the computed wave vectors for the axial and circumferential position of the ultrasound transducers 12b,c.

A measure of difference may be computed that is a sum of squares of absolute values of differences between the computed wave vectors and the Fourier coefficients, summed over the frequencies up to the bandwidth setting. In an embodiment, the differences may be weighted dependent on frequency. Equivalently a sum of squares of differences between predicted ultrasound vibration amplitudes and measured ultrasound vibration amplitudes may be used, combined with temporal low pass filtering of the time dependent amplitudes according to the bandwidth setting W, before and/or after taking the difference. The convergence criterion may be whether this measure of difference exceeds a predetermined threshold value.

The adaptation of the parameters of fifth step 45 involves applying position dependent updates to the thickness parameter values. Combinations of update sizes for different parameters, or updates of individual parameters are selected that affect the differences between the predictions and the detections within the bandwidth setting. Such combinations of update sizes or updates can be identified using the derivatives of the differences with respect to the available model parameters for the bandwidth setting, when these derivatives can be derived from the model. Prior art fitting processes provide for such selections. Typically, updates of wall thicknesses are selected at or near spiralling ray paths between pairs of ultrasound transducers 12b,c at which differences between predictions and detections are present. The updates may be selected according to any suitable optimization technique, for example according to the Levenberg Marquardt algorithm.

The adaptation of the parameters of fifth step 45 may concentrates on adaptation of parameters, or combinations of parameters, that have the largest effect on the prediction in the bandwidth setting. Derivatives of the measure of difference with respect to respective ones of the parameters may be computed to select such parameters. For example, thickness values may be updated only for a sub-sampled subset of sampled positions and interpolating the thickness between these positions.

When the bandwidth setting W is increased the parameter values obtained with less bandwidth setting W are used as initial values for computing the parameter values for the increased bandwidth setting. Thus, spatial details increasingly higher spatial resolutions are made available using respective comparisons over an increasingly wider response frequency band. The use of initial values obtained with less bandwidth setting reduces the risk that the process converges to a set of parameters that is only locally optimal.

The interpolation of the parameter values for different positions on pipe 10 may be performed in any convenient way. Interpolation with a linear function between positions for which parameter values are available may be used for example. Other interpolation functions may be used, such as polynomial interpolation functions using polynomial coefficients derived from parameter values at three or more positions on the wall. Other interpolation functions include sums of sine and cosine functions of the circumferential angle times an integer number. This corresponds to a Fourier series. In an embodiment the coefficients of a polynomial or a Fourier series or other function expansion are used as parameters instead of thickness values at discrete locations. In this case, the number of Fourier coefficients that is used in the fitting process may be varied dependent on the bandwidth setting.

In the embodiment of FIG. 2, a series of transducers is located in successive virtual rings around the pipe, at circumferential locations that lie along a line in the axial direction of the pipe, with groups of transducers on mutually opposite sides of a support that is attached to the pipe. Transmission and reception with transducers on mutually opposite sides of the support is used to determine pipe damage at the support.

In this embodiment, a model may be used that provides a thickness function, defining the thickness of the pipe wall as a function op position along the line of transducers in the axial direction and optionally also further thickness functions defining the thickness along a plurality of parallel lines adjacent to that line. Otherwise, a similar measurement process may be used, comprising iterations at successively higher bandwidths, each using the thickness function (and optional further thickness functions) from the iteration at the preceding lower bandwidth as an initial thickness function (and optional further thickness functions). In turn, each iteration comprises adapting the thickness function (and optional further thickness functions) to that predictions based on the thickness function (and optional further thickness functions) approximate the measured wave vectors at the nearest frequency at or below the bandwidth, or a combination of frequencies up to the bandwidth. At least in the iteration for the lowest frequency the prediction is computed using propagators of the type described in the preceding.

Figure 5:
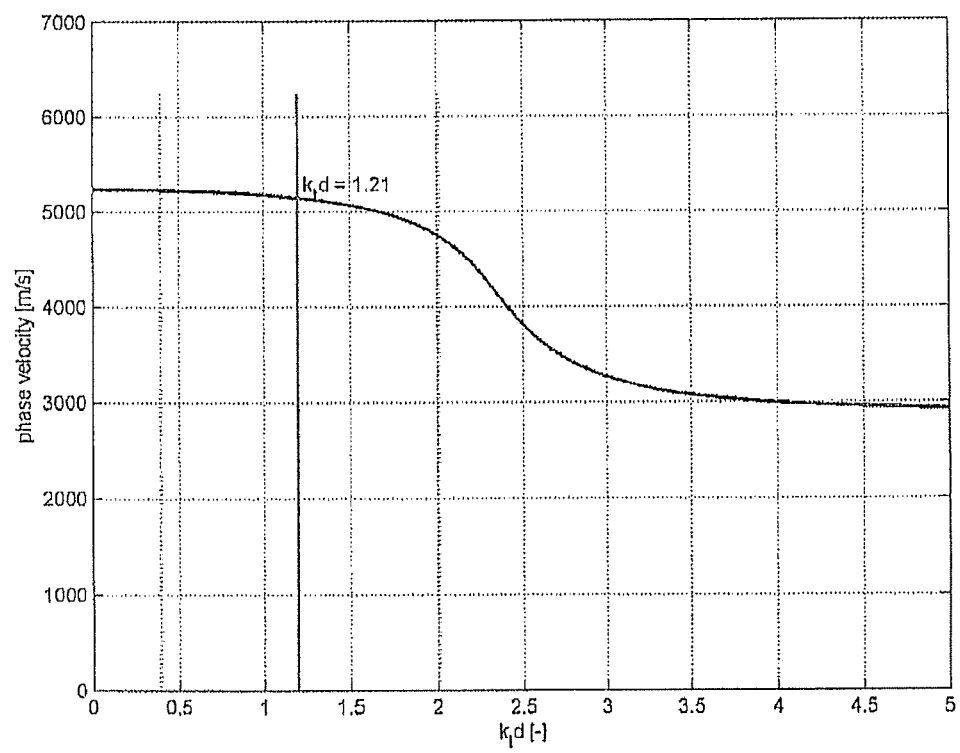
FIG. 5 shows a graph illustrating a relation between sound speed and wall thickness

Although an embodiment has been described that uses a model expressed in terms of pipe wall thickness as a function of position, from which the speed of sound for different frequencies can be derived, it should be appreciated that alternatively the model may define the speed of sound directly. In this case, the initialization of successive fitting processes may comprise determining the speed of sound at different positions for the next frequency from the previous speed of sound, for example by converting it temporarily to a thickness. Approximate formulas and tables relating thickness and speed of sound as a function of frequency, given bulk speed of sound, are known per se. FIG. 5 shows an example of sound speed (phase velocity) of a wall mode as a function of wall thickness (d is wall thickness divided by two and kt=2*pi*frequency/bulk shear wave speed).

The signal processing circuit may be implemented as a programmable computer circuit, combined with a program memory that contains instructions to make the programmable computer perform the described steps. Alternatively, part or all of the steps may be performed by dedicated circuits, designed to perform the steps. As used herein, statements that the signal processing circuit is configured to perform steps cover both the implementation with a programmable computer and dedicated circuits. A program for such a computer may be provided on a computer program product, such as a semi-conductor memory, a magnetic or optical disk, a signal modulated with information representing instructions, a tape etc.

The invention claimed is:

1. A method of performing ultrasonic pipeline wall property measurements, the method comprising
providing a set of ultrasound transmitters and a set of ultrasound receivers coupled to a pipeline at mutually different positions on the pipeline;
transmitting ultrasound signals from the ultrasound transmitters into a wall of the pipeline;
detecting the ultrasound response signals at the ultrasound receivers due to propagation of the ultrasound signals through the wall;
providing a first and second predictive model, defining predictions of the ultrasound response signals as a function of a first and second set of parameters that are determinative of position dependent ultrasound speed in the wall at a first and second spatial resolution at a first and second sound frequency, or sound frequencies up to the first and second frequency respectively, the second sound frequency being higher than the first sound frequency, the second spatial resolution being higher than the first spatial resolution, at least the first model defining predictions of wave vector values as a function of circumferential position in successive rings around the pipe as sums of wave vector values for a plurality of circumferential positions in a preceding one of the rings multiplied by propagation coefficients, using propagation coefficients that depend on the first set of parameters;
executing a first and second iterative fitting process, fitting a combination of values of the first and second set of the parameters to the detected ultrasound response signals according to the first and second predictive model respectively, the fitted combination of values of the first set being used to initialize the second set for the second iterative fitting process.

2. A method according to claim 1, comprising a series of predictive models, including the second predictive model as an initial predictive model in the series, each predictive model in the series defining predictions of the ultrasound response signals as a function of a respective set of parameters that are determinative of position dependent ultrasound speed in the wall at a respective spatial resolution at a respective sound frequency, or sound frequencies up to the respective sound frequency, the respective sound frequencies and the respective spatial resolutions increasing for successive further predictive models in the series;
executing successive iterative fitting processes, each fitting a combination of values of the respective set of parameters of a successive one of the further predictive models to the detected ultrasound response signals according to the successive one of the further predictive models respectively, the values for each next successive fitting process being initialized using the fitted combination of values from a preceding one of the successive fitting processes.

3. A method according to claim 1, wherein the second predictive model defines predictions of the ultrasound response signals by defining ray paths between transmitters and transducers and integrating travel times along the paths dependent on the position dependent ultrasound speed determined by the second set of parameters.

4. A method according to claim 1, wherein said first and second fitting process comprise minimizing a difference between ultrasound amplitudes of a predicted ultrasound response and a detected ultrasound response.

5. A method according to claim 1, wherein the pipeline has a bent section between the ultrasound transmitters and the ultrasound transmitters.

6. A method according to claim 1, wherein the transmitters and receivers are coupled to the pipeline along a first and second circumferential ring in planes transverse to an axial direction of the pipeline respectively, in each of the first and second ring at mutually spaced circumferential positions.

7. A method according to claim 1, wherein the pipeline is supported by a support having a contact with the pipeline, the transmitters and receivers being coupled to the pipeline at mutually spaced circumferential positions along an line in the axial direction of the pipeline, transmitters and receivers being coupled to the pipeline on mutually opposite sides of the contact respectively.

8. A method according to claim 1, wherein the transmitted ultrasound signals are wideband signals comprising components at both the first and second frequencies, the first and second fitting process being applied to selected frequency components of the detected ultrasound response signals.

9. A system for performing ultrasonic pipeline wall property measurements, the system comprising
  a set of ultrasound transmitters and a set of ultrasound receivers for coupling to a pipeline at mutually different positions on the pipeline;
  an excitation and detection circuit coupled to the transmitters and receivers;
  a signal processing circuit coupled to the excitation and detection circuit to receive response signals due to ultrasound transmission between pairs of transmitters and receivers, the signal processing circuit being configured to perform a first and second iterative fitting process, fitting a combination of values of a first and second set of a first and second predictive model to the detected ultrasound response signals respectively, the fitted combination of values of the first set being used to initialize the second set for the second iterative fitting process, wherein the first and second predictive model define predictions of the ultrasound response signals as a function of the first and second set of parameters that are determinative of position dependent ultrasound speed in the wall at a first and second spatial resolution at a first and second sound frequency, or sound frequencies up to the first and second frequency respectively, the second sound frequency being higher than the first sound frequency, the second spatial resolution being higher than the first spatial resolution, at least the first model defining predictions of a wave vector values as a function of circumferential position in successive rings around the pipe as sums of wave vector value for a plurality of circumferential positions in a preceding one of the rings multiplied by propagation coefficients, using propagation coefficients that depend on the first set of parameters.

10. A system according to claim 9, wherein the signal processing circuit is configured to use a series of predictive models, including the second predictive model as an initial predictive model in the series, each predictive model in the series defining predictions of the ultrasound response signals as a function of a respective set of parameters that are determinative of position dependent ultrasound speed in the wall at a respective spatial resolution at a respective sound frequency, or sound frequencies up to the respective sound frequency, the respective sound frequencies and the respective spatial resolutions increasing for successive further predictive models in the series, the signal processing circuit being configured to execute successive iterative fitting processes, each fitting a combination of values of the respective set of parameters of a successive one of the further predictive models to the detected ultrasound response signals according to the successive one of the further predictive models respectively, the values for each next successive fitting process being initialized using the fitted combination of values from a preceding one of the successive fitting processes.

11. A system according to claim 9, wherein the second predictive model defines predictions of the ultrasound response signals by defining ray paths between transmitters and transducers and integrating travel times along the paths dependent on the position dependent ultrasound speed determined by the second set of parameters.

12. A system according to claim 9, wherein the transmitters and receivers are located on the pipeline, the pipeline having a bent section between the ultrasound transmitters and the ultrasound transmitters.

13. A system according to claim 9, wherein the transmitters and receivers are coupled to the pipeline along a first and second circumferential ring in planes transverse to an axial direction of the pipeline respectively, in each of the first and second ring at mutually spaced circumferential positions.

14. A system according claim 9, wherein the pipeline is supported by a support having a contact with the pipeline, the transmitters and receivers being coupled to the pipeline at mutually spaced circumferential positions along an line in the axial direction of the pipeline, transmitters and receivers being coupled to the pipeline on mutually opposite sides of the contact respectively.

15. A computer program product, comprising a program of instructions for a programmable computer that, when executed by the computer will cause the computer to perform the method of claim 1.

* * * * *